United States Patent [19]

Theodoropulos

[11] Patent Number: 5,043,269

[45] Date of Patent: Aug. 27, 1991

[54] CHROMOGENIC SUBSTRATE TO PEROXIDASE ENZYMES

[76] Inventor: Spyros Theodoropulos, 2964 Hickory St., Yorktown Heights, N.Y. 10598

[21] Appl. No.: 156,210

[22] Filed: Feb. 16, 1988

[51] Int. Cl.$^5$ .............................................. C12Q 1/28
[52] U.S. Cl. .................................... 435/28; 435/12; 435/14; 435/192; 436/904; 534/649; 534/753; 534/770; 534/784; 534/789; 534/795
[58] Field of Search .................. 436/66, 903, 904; 435/12, 14, 28, 192; 534/649, 753, 770-773, 781-784, 787-789, 795

[56] References Cited

PUBLICATIONS

Geoghegan, W., "Adaptation of the Ngo-Lenhoff Peroxidase Assay for Solid Phase ELISA"; *J. of Immunol. Methods,* 60 (1983), 61-68.
Ngo, T., "A Sensitive and Versatile Chromogenic Assay for Peroxidase . . . ", *Anal. Biochem.,* 105 (1980), 389-397.
Kahn, V., "Tropolone as a Substrate for Horseradish Peroxidase", *Phytochemistry,* v. 24, No. 5 (1985), 909-913.
Schmid, P., "Differential Substrate Specificity of Isoperoxidases . . . ", *Angew. Botanik,* 62 (1988), 161-168.

*Primary Examiner*—Esther L. Kepplinger
*Assistant Examiner*—Carol A. Spiegel
*Attorney, Agent, or Firm*—Burgess, Ryan and Wayne

[57] ABSTRACT

A novel chromogenic substrate to peroxidase enzymes is provided which is comprised of a mixture of a colorless mixture of two compounds, such as, 3-methyl-2-benzothiazolinone hydrazone and 2-hydroxy-2,4,6-cycloheptatrienone, which undergo an oxidative coupling in the presence of peroxidase and hydrogen peroxide forming a purple indamine dye. Under certain circumstances the dye will precipitate out from the buffered solution and thus provide a permanent record of the determination. The mixture is also stable and unaffected by oxygen of the air or by hydrogen peroxide.

10 Claims, No Drawings

CHROMOGENIC SUBSTRATE TO PEROXIDASE ENZYMES

FIELD OF THE INVENTION

This invention relates, in general, to a unique chromogenic substrate to peroxidase enzymes. In one aspect, this invention is directed to a chromogenic substrate comprised of a colorless mixture of two compounds, such as, 3-methyl-2-benzothiazolinone hydrazone and 2-hydroxy-2,4,6-cycloheptatrienone, which undergo an oxidative coupling in the presence of peroxidase and hydrogen peroxide forming a purplish dye. In another aspect, this invention relates to a process for the preparation and use of the chromogenic substrate in a variety of qualitative and quantitative determinations of peroxidase in biological substances. The invention also is directed to the determination of biological components through peroxidase activity. Under certain conditions, the dye formed upon the oxidative interaction with peroxidase and hydrogen peroxide precipitates, thus forming a permanent record of the determination. Additionally, the chromogen substrate of the present invention also exhibits excellent photochemical stability against ultraviolet light and is not effected by either hydrogen peroxide or peroxidase alone, thus simplifying its commercial application.

BACKGROUND OF THE INVENTION

A variety of chromogenic substrates to peroxidase have been reported in the literature as being useful analytical techniques for the detection and measurement of peroxidase activity. Analytical techniques utilizing peroxidase or peroxidase coupled to antibodies and other molecules serve in the measurement of biological properties and components of compounds of interest. Typical components include among others glucose, maltose, bacteria, viruses, enzymes, drugs, hormones and the like for example, it is known that chromogenic substrates such as benzidine, O-tolidine, O-toluidine, and compounds such as 3-methyl-2-benzothiazolinone hydrazone and 3-(dimethylamino)benzoic acid can be used to monitor peroxidase activity. However, certain of these compounds have been shown to be carcinogenic and very sensitive to light, oxygen from the air and hydrogen peroxide.

In an article by T. T. Ngo and H. M. Lenhoff, Analytical Biochemistry, 105, 389–397 (1980), a chromogenic assay for peroxidase and peroxidase-coupled reactions is disclosed and it is indicated that the assay is sensitive and versatile. This assay is based on the oxidative coupling of 3-methyl-2-benzothiazolinone hydrazone and 3-(dimethylamino)benzoic acid. In the presence of hydrogen peroxide and the aforementioned two compounds, peroxidase catalyzes the formation of a deep purple compound, most likely an indamine dye, which has a broad absorption band between 575 and 600 nm with a peak at 590 nm. Using this assay system solutions of peroxidase can be determined in picomolar amounts by either a rate or a fixed-time method.

In the Journal of Immunological Methods, 60, 61–68 (1983) W. D. Geoghegan et al reported the use of the above Ngo-Lenhoff peroxidase assay for solid phase ELISA. While acknowledging the extreme sensitivity of the method and the rapid production of the indamine dye from the chromogen, the authors indicated that problems were encountered in the adaption of the assay to ELISA, for example, the blank developed color, exposure to light resulted in increased dye production, and other problems. However, by the use of various buffer systems, citric acid, and the like, it was possible for the authors to utilize the Ngo-Lenhoff assay for solid phase ELISA.

Nothwithstanding the sensitivity and versatility of the Ngo-Lenhoff method, a chromogenic substrate would be desirable which could provide a permanent record of the determination, exhibit excellent stability against ultraviolet light, and which would not be affected by either hydrogen peroxide or peroxidase alone. It was observed that the presence of hydrogen peroxide alone was detrimental to the Ngo-Lenhoff assay.

Accordingly, one or more of the following objects will be achieved by the practice of the present invention. It is an object of this invention to provide a chromgenic substrate which is useful in the quantitative and qualitative determination of peroxidase in biological substances, particularly biological fluids. Another object of this invention is to provide a novel indamine dye which can be formed by the reaction of readily available starting materials. A still further object of the present invention is to provide a unique chromogenic substrate to peroxidase which forms upon oxidative interaction a dye which can easily be observed by the naked eye, or determined qualitatively or quantitatively by absorption. Another object of this invention is to provide a substrate to peroxidase which exhibits superior stability against untraviolet light, oxygen of the air, and hydrogen peroxide. It is also an object of this invention to provide a substrate to peroxidase which upon oxidative interaction forms an indamine dye which can precipitate forming a permanent record of the assay. A still further object of this invention is to provide a method for detecting peroxidase activity in biological samples or immunodiagnostic formats involving peroxidase by employing the substrate of the present invention. These and other objects will readily become apparent to those skilled in the art in the light of the teachings herein set forth.

SUMMARY OF THE INVENTION

The present invention relates to a novel chromogenic substrate to peroxidase, a process for its preparation, and its use in determining peroxidase in biological substances.

The chromogenic substrate is comprised of a colorless mixture of a hydrazone of formula I:

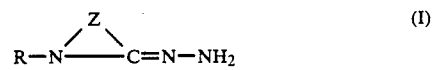

and a 2-hydroxy-2,4,6-cycloheptatrienone of formula II:

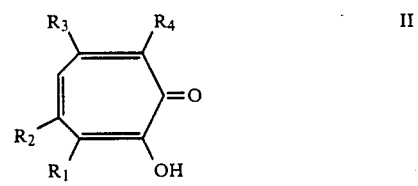

When the mixture of I and II interacts with peroxidase in the presence of hydrogen peroxide, an oxidative coupling occurs between I and II forming a purple to blue indamine dye III which can easily be determined qualitatively or quantitatively:

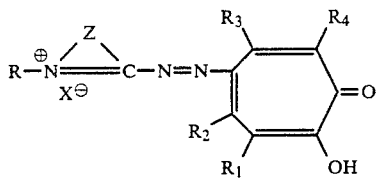

wherein R, $R_1$, $R_2$, $R_3$, $R_4$, X and Z are as hereinafter indicated. By utilizing the above mixture, the developed dye serves as an indicator allowing a qualitative or quantitative determination of peroxidase.

DETAILED DESCRIPTION OF THE INVENTION

As indicated above, the chromogenic substrate to peroxidase enzymes of formula III is prepared by the reaction of a hydrazone of formula I and a 2-hydroxy-2,4,6-cycloheptatrienone of formula II. In the chromogen substrate R represents a group containing from 1 to 25, and more preferably, 1 to 12 carbon atoms and includes an alkyl group, e.g., methyl, ethyl, n-propyl, isobutyl, n-amyl, isoamyl, and the like; an alkenyl group. e.g., allyl, methallyl, and the like; an aralkyl group, e.g., benzyl, phenethyl and the like; an alkoxyalkyl group, e.g., methoxyethyl, ethoxyethyl, and the like; an aryloxyalkyl group, e.g., phenoxymethyl, phenoxyethyl, and the like; a hydroxyalkyl group, e.g., hydroxymethyl, hydroxyethyl, betahydroxypropyl, and the like; a carboxyalkyl group, e.g., carboxymethyl, carboxyethyl, carboxypropyl, and the like; a carboalkoxyalkyl group, e.g., carbomethoxymethyl, carbomethoxyethyl, carboethoxyethyl, acetoxyethyl, acetoxypropyl, and the like; an arylthioalkyl group, e.g., phenylmercaptomethyl, phenylmercaptoethyl, and the like; a sulfohylalkyl group, e.g., sulfonic acid butyl, and the like; $R_1$-$R_4$ represent hydrogen, halogen, NO, $NO_2$, $SO_3H$,
  COOH, or a group containing from 1 to 25 and more preferably 1 to 12 carbon atoms, and can be a substituted or unsubstituted alkyl, alkoxy, aryl, heteroaryl, aryloxy, and the like.

X represents an anion selected from the group consisting of F, Cl, Br, I, acetate, phthalate, phosphate, citrate, borate, sulfate and nitrate; and Z represents a group containing non-metallic atoms necessary to complete a heterocyclic or heterobicyclic ring with the atoms to which it is attached. Preferably, Z contains carbon, oxygen or sulfur and up to a total of 25 and more preferably, up to 18 carbon atoms. Z can also be substituted with one or more substituents selected from the group consisting of lower alkyl, nitro, halogen, carboxyl, sulfonyl, amino and diamino groups.

In a preferred embodiment of the present invention, the chromogenic substrate is formed from a mixture of 3-methyl-2-benzothiazolinone hydrazone hydrochloride IV and 2-hydroxy-2,4,6-cycloheptatrienone V

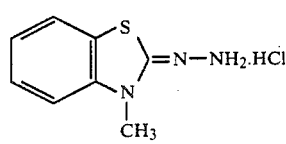

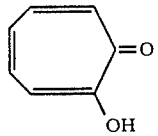

These compounds undergo an oxidative coupling in the presence of peroxidase and hydrogen peroxide to form an indamine dye having the general formula VI

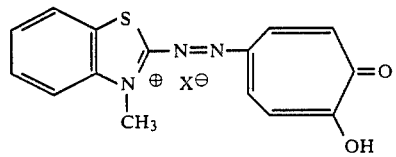

wherein X is as indicated above. The product formed is a purple to blue dye which absorbs at 540 nm. The developed dyes serve as an indicator allowing a qualitative or quantitative determination of peroxidase in biological fluids and other immunodiagnostic formats.

In general, a biological sample containing peroxidase enzymes such as, for example, horseradish peroxidase, develops a red to purple color when a mixture of IV and V, and hydrogen peroxide is added. The red to purple color which develops upon the oxidative interaction of IV and V is due to formation of the indamine dye VI. The dye under certain conditions involving an aqueous solution, precipitates from the reaction mixture forming a permanent record. Furthermore, a mixture of IV and V in buffer solutions in which hydrogen peroxide has been added remains unchanged without the development of any color. Only upon addition of the peroxidase, does the colored dye develop, thus revealing the presence of peroxidase activity.

The molar ratios of I and II in buffer solutions may vary from equal molar, to 1 mol of I and up to 100 moles of II or 1 mol of II and up to 100 moles of I with the preferred molar ratio being 10 mols of I and 1 mol of II.

The buffers constituting the solutions of the mixture of I and II among others are phosphate, citrate, saline, borate, phthalate or combination of more than one with the preferred buffer being citric acid-dibasic sodium phosphate, pH 7.0 buffer.

The chromogenic substrates to peroxidase of the present invention are useful in a wide variety of areas, as a biochemical tool for the detection and measurement of peroxidase activity in biological samples and in the detection and measurements of biological components. For example, the chromogenic substrates of the present invention due to their stability against hydrogen peroxide, light, and oxygen of the air can be employed in immunodiagnostic assays involving pairs of antibodies, one bound to a solid phase and the other labeled with peroxidase to permit detection. Due to the unique characteristics of precipitating from buffer solution, this substrate can be employed in the development of positive-negative immunoassays leaving a permanent record of the determination.

The substrate of the present invention is also useful in systems involving labeled avidin/strepavidin and biotinylated antibodies employed in histochemistry and other diagnostic formats. As previously indicated, the chromogenic substrates of this invention are ideal agents due to their photochemical stability and their stability against oxygen of the air and hydrogen peroxide. This is in addition to the precipitating property of the chromogen formed during the oxidative interaction which makes these substrates useful in a variety of applications where peroxidases are involved.

The following examples illustrate the best mode presently contemplated for the practice of this invention.

EXAMPLE 1

Preparation of Horseradish Peroxidase in Buffer Solution 1 milligram of horseradish peroxidase was dissolved in 100 milliliters of phosphate-saline buffer prepared by diluting 2.76 grams of sodium phosphate (monobasic), 11.36 grams of sodium phosphate (dibasic) and 1.8 grams of sodium chloride to 1 liter with distilled water.

EXAMPLE 2

Preparation of Urea Peroxide Buffer Solution 50 milligrams of urea peroxide was dissolved in 100 milligrams of phosphate-citric acid buffer (pH 7.0) prepared by diluting 500.0 milliters of 0.2M sodium phosphate (dibasic) with 120 milliliters 0.1M citric acid to 1 liter with distilled water.

EXAMPLE 3

Preparation of Indamine Dye 150 milligrams of 3-methyl-2-benzothiazolinone hydrazone hydrochloride and 200 milligrams (excess) of 2-hydroxy-2,4,6-cycloheptatrienone dissolved in 100 milliliters of phosphate-citric acid buffer prepared by diluting 120 milliliters of 0.1M citric acid and 500 milliliters of 0.2M dibasic sodium phosphate to 1 liter with distilled water. To this was added 4milliliters of urea peroxidase solution prepared as in Example 2 and 2 milliliters of horseradish peroxidase prepared as in Example 1 and the mixture stirred for two hours.

The dye formed was filtered and washed with water. Recrystallization from methanol gave 50 milligrams of the indamine dye. Absorption in methanol showed peaks at 537, 358, 306 and 267 nm. NMR (CDCl$_3$) TMS internal standard showed peaks at 7.8 (m, 8H, aromatic); 6.5(m, 5H, citric acid); and 2.75 (m, 3H, CH$_3$—N+)PPM.

EXAMPLE 4

Preparation of Chromogen Substrate 120 milligrams of 2-hydroxy-2,4,6-cycloheptatrienone (HCT) was dissolved in 10.0 milliliters of phosphate-citric acid buffer pH 7.0 prepared by diluting 20 milliliters of 0.1M citric acid and 500 milliliters of 0.2M dibasic sidium phosphate to 1 liter with distilled water, 215 milligrams of 3-methyl-2-benzothiazolinone hydrazone hydrochloride (MBH) was dissolved in 10 milliliters of the same phosphate-citric acid buffer.

The chromogen substrate solution was then prepared by mixing one part of HCT solution with one part of MBH solution and eight parts of the urea peroxide buffer solution pH 5.5 as prepared in Example 2.

EXAMPLE 5

Streptoccocus Group A Immunoassay

Reagents to perform a sandwich immunoassy for Strep A were obtained from a commercial source.

To Strep A antibody bound to a plastic device (paddle) was added positive Strep A control. Antibody labeled with horseradish peroxidase was then added and allowed to incubate for two minutes at ambient temperature. The paddle was then washed with tap water for one minute to remove unbound material. To the paddle was then added the chromogen substrate mixture of example 4 and incubated at ambient temperature for two minutes. A positive sample gave a reddish-purple color. The paddle was washed with tap water for one minute leaving a permanent red-violet color that remained fixed to the paddle.

Although the invention has been illustrated by the preceding examples it is not to be construed as being limited to the materials employed therein, but rather, the invention relates to the generic area as hereinbefore disclosed. Various modifications and embodiments can be made without departing from the spirit or scope thereof.

What is claimed is:

1. A chromogenic substrate for peroxidase comprising a mixture of:

(a) a hydrazone compound of the formula:

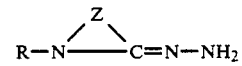

and (b) a 2-hydroxy-2,4,6-cycloheptatrienone compound of the formula:

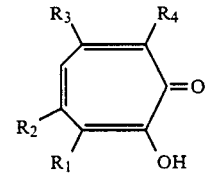

wherein:

R represents a group containing from 1 to 25 carbon atoms and is selected from the group consisting of alkyl, alkenyl, aralkyl, hydroxyalkyl, alkoxyalkyl, aryloxyalkyl, carboxyalkyl, carboalkoxyalkyl, arylthioalkyl, suflonalkyl;

$R_1$–$R_4$ represent hydrogen, halogen, NO, NO$_2$, SO$_3$H, COOH, or a group containing from 1 to 25 carbon atoms which can be substituted or unsubstituted alkyl, alkoxy, aryl, heteroaryl or aryloxy; X represents an anion selected from the group consisting of F, Cl, Br, I, acetate, phthalate, phosphate, citrate, borate, sulfate and nitrate; and Z represents a group containing non-metallic atoms necessary to complete a heterocyclic or heterobicyclic ring with the atoms to which it is attached and contains at least one member selected from the group consisting of oxygen and sulfur and up to a total of 25 carbon atoms, and can be substituted with one or more substituents selected from the group consisting of lower alkyl, nitro, halogen, carboxyl, sulfonyl, amino and diamino groups.

2. The chromogenic substrate of claim 1 wherein R is lower alkyl and at least one of $R_1$–$R_4$ is lower alkyl with the other groups being hydrogen.

3. The chromogenic substrate of claim 1 wherein R is lower alkyl and $R_1$–$R_4$ are hydrogen.

4. The chromogenic substrate of claim 1 wherein R is methyl and $R_1$–$R_4$ are hydrogen.

5. The chromogenic substrate of claim 1 wherein Z contains at least one oxygen atom.

6. The chromogenic substrate of claim 1 wherein Z contains at least one sulfur atom.

7. The chromogenic substrate of claim 1 wherein the hydrazone compound is 3-methyl-2-benzothiazolinone hydrazone hydrochloride.

8. The chromogenic substrate of claim 1 wherein the hydrazone compound is 3-methyl-2-benzothiazolinone hydrazone hydrochloride and the cycloheptatrienone compound is 2-hydroxy-2,4,6-cycloheptatrienone.

9. An analytical method for the detection of peroxidase in a biological substance which comprises contacting said biological substance with chromogenic substrate therefore said peroxidase comprising, the mixture of claim 1 to form an indamine dye; and, detecting said indamine dye to detect said peroxidase in said biological sample.

10. The method of claim 9 wherein the mixture comprises 3-methyl-2-benzothiazolinone hydrochloride and 2-hydroxy-2,4,6-cycloheptatrienone.

* * * * *

UNITED STATES PATENT AND TRADEMARK OFFICE
CERTIFICATE OF CORRECTION

PATENT NO.   : 5,043,269
DATED        : August 27, 1991
INVENTOR(S)  : Spyros Theodoropulos It is certified that error appears in the above-identified patent and that said Letters Patent is hereby corrected as shown below:

Column 6, line 51-54;

delete "X represents an anion selected from the group consisting of F, Cl, Br, I, acetate, phthalate, phosphate, citrate, borate, sulfate and nitrate, "

Signed and Sealed this

Fifth Day of January, 1993

Attest:

DOUGLAS B. COMER

*Attesting Officer*      *Acting Commissioner of Patents and Trademarks*